United States Patent [19]

Mikami et al.

[11] Patent Number: 5,602,302
[45] Date of Patent: Feb. 11, 1997

[54] MODELS FOR ASTHMA GUINEA PIG

[75] Inventors: Hiroki Mikami; Ryoji Nishibata, both of Hyogo, Japan

[73] Assignee: Nippon Zoki Pharmaceutical Co., Ltd., Osaka, Japan

[21] Appl. No.: 175,740

[22] Filed: Dec. 30, 1993

Related U.S. Application Data

[63] Continuation of Ser. No. 796,258, Nov. 19, 1991, abandoned.

[30] Foreign Application Priority Data

Nov. 21, 1990 [JP] Japan ..................... 2-319705

[51] Int. Cl.$^6$ .................. C12N 15/00; A61K 49/00
[52] U.S. Cl. ............ 800/2; 800/DIG. 4; 424/9.1; 435/172.3
[58] Field of Search ............. 800/2, DIG. 4; 424/9, 9.1; 435/172.3

[56] References Cited

PUBLICATIONS

Watanabe (1980) Atherosclerosis 36, 261–268.
Ayitey–Smith (1974) J. Pharm. Pharmac. 26, 208–209.

*Primary Examiner*—Deborah Crouch
*Attorney, Agent, or Firm*—Fisher, Christen & Sabol

[57] ABSTRACT

The present invention relates to a method of preparing bronchial hypersensitive or hyposensitive guinea pigs by selective breeding on the basis of bronchial sensitivity to inhalant chemicals inducing bronchoconstriction. The hypersensitive guinea pigs of the present invention are extremely useful as model animals for the study of bronchial asthma and allergic rhinitis and for the evaluation of efficacy of-antiasthmatics and antiallergic substances.

24 Claims, 1 Drawing Sheet

MODELS FOR ASTHMA GUINEA PIG

This application is a continuation of application Ser. No. 07/796,258, filed Nov. 19, 1991, now abandoned.

BACKGROUND OF THE INVENTION

The present invention relates to a method of preparing novel model animals for asthma with constant bronchial hyper- or hyposensitivity.

Since bronchial sensitivity in asthma patients is accelerated, there is a need of diagnosis of asthma by measuring degree of bronchial sensitivity as an indication of severity of asthmatic symptom. Therefore, a development of model animals with bronchial hypersensitivity is hoped for the study of human bronchial asthma.

In various experimental animals, guinea pigs have bronchial hypersensitivity and so allergic reaction can be easily induced. Generally, guinea pigs have been widely used as allergic and asthmatic model animals.

However, there is a wide range of individual difference in bronchial sensitivity of guinea pigs, and breeding of guinea pigs is difficult because of the longer duration of pregnancy and smaller litter size compared with rats and mice. Also because of the tendency toward inbreeding depression, it is extremely difficult to establish a strain of guinea pigs as animal models for human diseases. Therefore, the strain of guinea pigs with constant hypersensitivity has not been established yet.

DETAILED DESCRIPTION OF THE INVENTION

Figure 1:
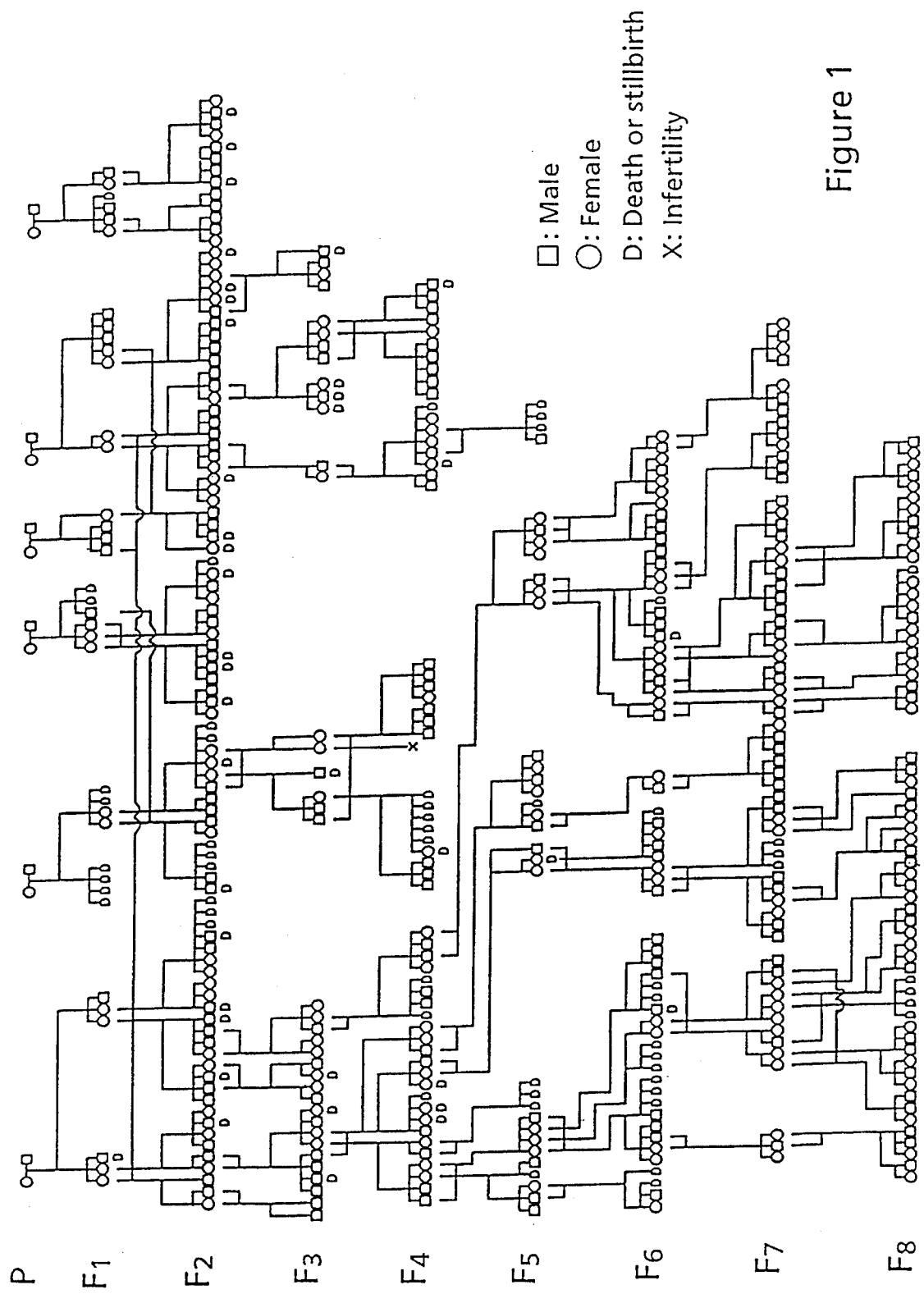
FIG. 1 illustrates the pedigree of bronchial hypersensitive guinea pigs until the $F_8$ generation.

An object of the invention is to provide a method of preparing model animals for asthma with bronchial hypersensitivity and the other with hyposensitivity as a control. Another object of this invention is to provide novel model animals for asthma with constant bronchial hypersensitivity prepared by the said method.

The present invention relates to a method of preparing model animals for asthma with constant bronchial hyper- or hyposensitivity by selective breeding on the basis of bronchial sensitivity to inhalant chemicals inducing bronchoconstriction.

The inventor selected guinea pigs in various experimental animals to prepare model animals for human bronchial asthma, because guinea pigs have bronchial hypersensitivity and so allergic reaction can be easily induced. In several existing strains of guinea pigs, Hartley-strain guinea pigs are most available and preferable, because the individual difference in bronchial sensitivity of Hartley-strain guinea pigs is very wide and so it is easy to form an original colony of bronchial hyper- or hyposensitive lines. The bronchial sensitivity of the Hartley-strain guinea pigs is slightly changed with age, but the animals show constant bronchial sensitivity after eight weeks of age, and there is small deference between male and female in bronchial sensitivity.

A chemical having bronchoconstrictive effect, which is used in the usual measurement test of bronchial sensitivity, such as histamine, acetylcholine, methacholine, serotonin, prostaglandin Fla, prostaglandin $F_2\alpha$, leukotriene $C_4$, leukotriene $D_4$, SRS-A or PAF, can be employed in the present invention as an inhalant chemical.

There are various methods of measuring bronchial sensitivity to the said chemicals inducing bronchoconstriction, such as a method measuring of constrictive reaction of extirpated airway and the like.

In the case of using guinea pigs which are difficult to breed as mentioned above, it is a preferable method to measure bronchial sensitivity under the condition that the animals are kept alive in order to prevent a decrease of the number of animals in the line. For example, the method of the present inventors [Inhalation method: Exp. Anim. 38(2), 107–118 (1989)] can be employed, i.e. an inducing chemical such as acetylcholine or histamine is inhaled to the animals, and then the time interval from the start of inhalation to prostration is measured (this time is abbreviated as TNPFD "Time Needed to Produce Falling Down"). This inhalation method can be used as one of preferable methods, bronchial sensitivity can be measured quantitatively, and also that keeps the animals alive to be used for further breeding.

To measure bronchial sensitivity to an inhalant chemical inducing bronchoconstriction quantitatively, for example, there is a method to find a dose threshold by gradually increasing dose of an inhalant chemical. However, this method requires many times of the test and so takes longer. It is difficult to measure bronchial sensitivity of many animals.

With regard to the said inhalation method, a correlation was confirmed between the TNPFD and dose threshold of bronchial sensitivity. It is a preferable method actually that an inducing chemical with a settled concentration is inhaled to the animals and then bronchial sensitivity to the inhalant chemical is measured on the basis of the TNPFD. This method takes a small number of tests. The concentration of the used chemical and the standard value for selection of bronchial hyper- and hyposensitive lines can be suitably settled. For example, a mean TNPFD is measured, and on the basis of the mean time, guinea pigs with a TNPFD of under two thirds of the mean TNPFD is regarded as bronchial hypersensitive animals, and the guinea pigs with a TNPFD of not less than one and a half as long as the mean TNPFD is regarded as bronchial hyposensitive animals.

The bronchial hyper- and hyposensitive guinea pigs of the present invention can be prepared by repeated passage selections, i.e. guinea pigs with similar bronchial sensitivity are basically crossbred with each other. Generally, it is preferable to use brother-sister mating fully, which can increase coefficient of inbreeding sharply. However, in the case of guinea pigs, because of the tendency toward inbreeding depression and smaller litter size compared with other animals, cousin mating and selective mating such as cross breeding without blood relationship among animals with similar bronchial sensitivity are properly added to basic brother-sister mating to prevent extinction of the pedigree of guinea pigs in the present invention.

EXAMPLES (1) Measurement of bronchial sensitivity to acetylcholine or histamine Bronchial sensitivity to acetylcholine or histamine was measured according to the inhalation method as mentioned above.

Each guinea pig was placed in a glass receptacle (volume; 10 l), and exposed to acetylcholine or histamine, which is dissolved in physiological saline just prior to use, using a glass nebulizer (nebulizing volume; 0.1 ml/min) connected to a compressor (air delivery; 6 l/min). The bronchial sensitivity was evaluated on the basis of the time interval from the start of inhalation to prostration caused by dyspnea.

(2) Evaluation of bronchial hyper- or hyposensitivity

Bronchial sensitivity was evaluated on the basis of a TNPFD of guinea pigs by exposure to 0.08% acetylcholine and 0.025% histamine. The TNPFD to 0.08% acetylcholine and 0.025% histamine was 377±33 seconds and 233±9.5 seconds (mean±standard error), respectively, in the original strain (P). Therefore, guinea pigs with a TNPFD of under 250 seconds to acetylcholine and under 150 seconds to histamine were regarded as bronchial hypersensitive animals, while those with a TNPFD not less than 600 seconds to acetylcholine and 350 seconds to histamine were regarded as bronchial hyposensitive animals.

(3) Preparation of bronchial hypersensitive or hyposensitive guinea pigs (Mating system)

Four-week-old SPF Hartley-strain guinea pigs of both sexes (30 males and 30 females) were purchased to form a original colony. Eight-week-old guinea pigs can be used, because it was confirmed that the animals showed constant bronchial sensitivity after this age by the said inhalation method. The bronchial sensitivity was measured, first to acetylcholine (8 weeks old) and then to histamine (9 weeks old), and 10-week-old guinea pigs were used for selective breeding.

The breeding was carried out by basically using brother-sister mating which can increase coefficient of inbreeding sharply. In the present invention, cousin mating and selective mating such as cross breeding without blood relationship were properly added to prevent extinction of the pedigree of guinea pigs, though coefficient of inbreeding increases slowly.

As an example, the pedigree of bronchial hypersensitive guinea pigs is shown in FIG. 1.

Tables 1 and 2 show changes in appearance rates for bronchial sensitivity in hyper- and hyposensitive lines in each generation.

In the figure and tables in this specification, parent guinea pigs in the original strain are abbreviated to "P", and guinea pigs in from the first to eighth generations are abbreviated to from "$F_1$" to "$F_8$", respectively. And also acetylcholine and histamine are abbreviated to "ACh" and "Hist", respectively.

TABLE 1

| | appearance rates for bronchial hypersensitive guinea pigs | |
|---|---|---|
| | ACh (%) | Hist (%) |
| [P] | 3 | 3 |
| [$F_1$] | 30 | 30 |
| [$F_2$] | 59 | 33 |
| [$F_3$] | 80 | 48 |
| [$F_4$] | 98 | 81 |
| [$F_5$] | 100 | 90 |
| [$F_6$] | 100 | 100 |
| [$F_7$] | 100 | 100 |
| [$F_8$] | 100 | 100 |

TABLE 2

| | appearance rates for bronchial hyposensitive guinea pigs | |
|---|---|---|
| | ACh (%) | Hist (%) |
| [P] | 10 | 3 |
| [$F_1$] | 11 | 12 |
| [$F_2$] | 45 | 57 |
| [$F_3$] | 58 | 73 |
| [$F_4$] | 61 | 77 |

TABLE 2-continued

| | appearance rates for bronchial hyposensitive guinea pigs | |
|---|---|---|
| | ACh (%) | Hist (%) |
| [$F_5$] | 100 | 100 |
| [$F_6$] | 100 | 100 |
| [$F_7$] | 100 | 100 |
| [$F_8$] | 100 | 100 |

According to the method of Lush et al. (Lush's 0–1 method), realized heritabilities were calculated from the appearance rates of bronchial hyper- or hyposensitive guinea pigs on the basis of the TNPFD, which are shown in Table 3.

TABLE 3

| | hypersensitive guinea pigs | | hyposensitive guinea pigs | |
|---|---|---|---|---|
| | ACh | Hist | ACh | Hist |
| [$F_1$–$F_2$] | 0.34 | 0.14 | 0.48 | 0.66 |
| [$F_2$–$F_3$] | 0.35 | 0.21 | 0.30 | 0.25 |
| [$F_3$–$F_4$] | 0.43 | 0.19 | 0.69 | 0.44 |

As shown in Tables 1 and 2, the appearance rates for bronchial hyper- and hyposensitive guinea pigs to acetylcholine and histamine increased with successive generations. In the both lines, the appearance rate in the $F_5$ generation was 90% or above, and that was 100% in the $F_6$ generation. The bronchial hyper- and hyposensitive lines derived from Hartley-strain guinea pigs can be established hereditarily.

Studies on biological characteristics in the bronchial hyper- and hyposensitive guinea pigs were undertaken, and the following results were obtained.

(1) Airway resistance to intravenously administered acetylcholine, histamine and leukotriene $D_4$ was found to be different between the bronchial hyper- and hyposensitive guinea pigs. Airway resistance of the hypersensitive guinea pigs to the inducing chemicals was increased compared with those of the hyposensitive animals.

(2) The number of muscarinic acetylcholine receptors in lung membrane preparation and its affinity increased significantly in the hypersensitive animals compared with the hyposensitive animals.

(3) Relative percentage of lymphocytes and eosinophils was significantly higher in the hypersensitive animals than in the hyposensitive animals.

In various experimental animals, bronchial sensitivity of guinea pigs is very accelerated, and so guinea pigs have been widely used as allergic and asthmatic model animals, but there is a wide range of individual difference in bronchial sensitivity. It has been hoped of the establishment of model animals with constant bronchial hypersensitivity to chemicals inducing bronchoconstriction such as histamine, acetylcholine and the like.

However, the breeding of guinea pigs is difficult because of the longer duration of pregnancy (about 60 days) and smaller litter size. Also because of the tendency toward inbreeding depression, a strain of guinea pigs with constant bronchial hypersensitivity has not been established yet.

In consideration of the difficulty of breeding of guinea pigs, the inhalation method was adopted in the present invention. Namely, a chemical inducing bronchoconstriction such as acetylcholine or histamine was inhaled to guinea pigs, and then the time interval from the start of inhalation to prostration caused by dyspnea (TNPFD) was measured.

This inhalation method can keep guinea pigs alive to be used for further breeding, in order to prevent a decrease of the number of animals and extinction of the pedigree of guinea pigs.

Previously it was reported that bronchial hyper- and hyposensitive guinea pigs had been developed by passage breeding with only brother-sister mating. However, probably the breeding was not continued because of inbreeding depression and small size of the original colony. The final report was concerned with the $F_2$ generation and thereafter there was no report that such model animals for asthma had been established.

In the present invention, cousin mating and selective mating without blood relationship were properly added to basic brother-sister mating in order to prevent inbreeding depression with sharp increase of coefficient of inbreeding. In addition, the inventors of the present invention adopted a method that passage selections were carried out with forming as larger colony as possible. Since the said method of the present invention does not give a sharp increase or decrease of bronchial sensitivity, longer breeding for many generations and a great many animals should be needed in the present invention.

As mentioned above, in bronchial hyper- and hyposensitive guinea pigs of the present invention, the appearance rates in the $F_5$ generation was 90% or above, and that was 100% in the $F_6$ generation. Namely, the inventors of the present invention can establish the bronchial hyper- and hyposensitive guinea pigs lines being available for further breeding.

The hypersensitive guinea pigs of the present invention show constant bronchial hypersensitivity to chemicals inducing bronchoconstriction such as acetylcholine, histamine and the like. Therefore, the hypersensitive guinea pigs are extremely useful as model animals for the study of bronchial asthma and allergic rhinitis and for the evaluation of efficacy of antiasthmatics and antiallergic substances.

The hyposensitive guinea pigs of the present invention are also useful as a contrary model animals to the hypersensitive guinea pigs and as a control of the hypersensitive line for the investigation of bronchial asthma.

What is claimed is:

1. Bronchial hypersensitive guinea pigs prepared by:
   (a) identifying guinea pigs with bronchial hypersensitivities to acetylcholine and histamine by measuring the time interval from the start of inhalation of acetylcholine and histamine by the guinea pigs to prostration of the guinea pigs caused by dyspnea, wherein the guinea pigs have bronchial sensitivities of less than 250 seconds to 0.08% acetylcholine and less than 150 seconds to 0.025% histamine, and
   (b) brother-sister mating or selectively mating with their cousins or unrelated guinea pigs those hypersensitive guinea pigs identified in (a), so that the appearance rate for guinea pigs with said bronchial sensitivities is at least 90% in at least the fifth generation.

2. Bronchial hypersensitive guinea pigs prepared by:
   (a) identifying guinea pigs with bronchial hypersensitivities to acetylcholine or histamine by measuring the time interval from the start of inhalation of acetylcholine or histamine by the guinea pigs to prostration of the guinea pigs caused by dyspnea, wherein the guinea pigs have bronchial sensitivities of less than 250 seconds to 0.08% acetylcholine or less than 150 seconds to 0.025% histamine, and
   (b) brother-sister mating or selectively mating with their cousins or unrelated guinea pigs those hypersensitive guinea pigs identified in (a), so that the appearance rate for guinea pigs with said bronchial sensitivities is at least 90% in at least the fifth generation.

3. Bronchial hypersensitive guinea pigs of claim 1 or 2 wherein the mating is carried out so that the appearance rate for guinea pigs with said bronchial hypersensitivities is 100% in at least the sixth generation.

4. Bronchial hypersensitive guinea pigs of claim 3 which are Hartley-strain guinea pigs.

5. Bronchial hyposensitive guinea pigs prepared by:
   (a) identifying guinea pigs with bronchial hyposensitivities to acetylcholine and histamine by measuring the time interval from the start of inhalation of acetylcholine and histamine by the guinea pigs to prostration of the guinea pigs caused by dyspnea, wherein the guinea pigs have bronchial sensitivities not less than 600 seconds to 0.08% acetylcholine and not less than 350 seconds to 0.025% histamine, and
   (b) brother-sister mating or selectively mating with their cousins or unrelated guinea pigs those hyposensitive guinea pigs identified in (a), so that the appearance rate for guinea pigs with said bronchial sensitivities is at least 90% in at least the fifth generation.

6. Bronchial hyposensitive guinea pigs prepared by:
   (a) identifying guinea pigs with bronchial hyposensitivities to acetylcholine or histamine by measuring the time interval from the start of inhalation of acetylcholine or histamine by the guinea pigs to prostration of the guinea pigs caused by dyspnea, wherein the guinea pigs have bronchial sensitivities of not less than 600 seconds to 0.08% acetylcholine or not less than 350 seconds to 0.025% histamine, and
   (b) brother-sister mating or selectively mating with their cousins or unrelated guinea pigs those hyposensitive guinea pigs identified in (a), so that the appearance rate for guinea pigs with said bronchial sensitivities is at least 90% in at least the fifth generation.

7. Bronchial hyposensitive guinea pigs of claim 5 or 6, wherein the mating is carried out so that the appearance rate for guinea pigs with said bronchial hyposensitivities is 100% in at least the sixth generation.

8. Bronchial hyposensitive guinea pigs of claim 7 which are Hartley-strain guinea pigs.

9. A method of preparing guinea pigs hypersensitive to inhalant-chemical induced bronchoconstriction, wherein the method comprises:
   (a) identifying guinea pigs with bronchial hypersensitivities to acetylcholine and histamine by measuring the time interval from the start of inhalation of acetylcholine and histamine by the guinea pigs to prostration of the guinea pigs caused by dyspnea, wherein the guinea pigs have bronchial sensitivities of less than 250 seconds to 0.08% acetylcholine and less than 150 seconds to 0.025% histamine, and
   (b) brother-sister mating or selectively mating with their cousins or unrelated guinea pigs those hypersensitive guinea pigs identified in (a), so that the appearance rate for guinea pigs with said bronchial sensitivities is at least 90% in at least the fifth generation.

10. A method of preparing guinea pigs hypersensitive to inhalant-chemical induced bronchoconstriction, wherein the method comprises:
    (a) identifying guinea pigs with bronchial hypersensitivities to acetylcholine or histamine by measuring the time interval from the start of inhalation of acetylcholine or histamine by the guinea pigs to prostration of the guinea pigs caused by dyspnea, wherein the guinea pigs have bronchial sensitivities of less than 250 seconds to 0.08% acetylcholine or less than 150 seconds to 0.025% histamine, and (b) brother-sister mating or selectively mating with their cousins or unrelated guinea pigs those hypersensitive guinea pigs identified in (a), so that the appearance rate for guinea pigs with said bronchial sensitivities is at least 90% in at least the fifth generation.

11. The method of claim 9 or 10, wherein the mating is carried out so that the appearance rate for guinea pigs with said bronchial hypersensitivities is 100% in at least the sixth generation.

12. A method of preparing guinea pigs hyposensitive to inhalant-chemical induced bronchoconstriction, wherein the method comprises:

(a) identifying guinea pigs with bronchial hyposensitivities to acetylcholine and histamine by measuring the time interval from the start of inhalation of acetylcholine and histamine by the guinea pigs to prostration of the guinea pigs caused by dyspnea, wherein the guinea pigs have bronchial sensitivities not less than 600 seconds to 0.08% acetylcholine and not less than 350 seconds to 0.025% histamine, and (b) brother-sister mating or selectively mating with their cousins or unrelated guinea pigs those hyposensitive guinea pigs identified in (a), so that the appearance rate for guinea pigs with said bronchial sensitivities is at least 90% in at least the fifth generation.

13. A method of preparing guinea pigs hyposensitive to inhalant-chemical induced bronchoconstriction, wherein the method comprises:

(a) identifying guinea pigs with bronchial hyposensitivities to acetylcholine or histamine by measuring the time interval from the start of inhalation of acetylcholine or histamine by the guinea pigs to prostration of the guinea pigs caused by dyspnea, wherein the guinea pigs have bronchial sensitivities of not less than 600 seconds to 0.08% acetylcholine or not less than 350 seconds to 0.025% histamine, and (b) brother-sister mating or selectively mating with their cousins or unrelated guinea pigs those hyposensitive guinea pigs identified in (a), so that the appearance rate for guinea pigs with said bronchial sensitivities is at least 90% in at least the fifth generation.

14. The method of claim 12 or 13, wherein the mating is carried out so that the appearance rate for guinea pigs with said bronchial hyposensitivities is 100% in at least the sixth generation.

15. The method of claim 9, 10, 12 or 13, wherein the guinea pigs are Hartley-strain guinea pigs.

16. The method of claim 10 or 13, wherein the chemical inducing bronchoconstriction is acetylcholine.

17. A method of preparing guinea pigs hypersensitive to inhalant-chemical induced bronchoconstriction, wherein the method comprises:

(a) identifying guinea pigs with bronchial hypersensitivities to an inhalant-chemical by measuring the time interval from the start of inhalation by the guinea pigs of the chemical inducing bronchoconstriction to prostration of the guinea pigs by dyspnea, wherein said guinea pigs have bronchial sensitivities less than two thirds of the mean of said measured time interval, and (b) brother-sister mating or selectively mating with their cousins or unrelated guinea pigs those hypersensitive guinea pigs identified in (a), so that the appearance rate for guinea pigs with said bronchial sensitivities is at least 90% in at least the fifth generation.

18. The method of claim 17, wherein the mating is carried out so that the appearance rate for guinea pigs with said bronchial hypersensitivities is 100% in at least the sixth generation.

19. The method of claim 17, wherein the guinea pigs are Hartley-strain guinea pigs.

20. The method of claim 17, wherein the chemical inducing bronchoconstriction is acetylcholine or histamine.

21. A method of preparing guinea pigs hyposensitive to inhalant-chemical induced bronchoconstriction, wherein the method comprises:

(a) identifying guinea pigs with bronchial hyposensitivities to an inhalant-chemical by measuring the time interval from the start of inhalation by the guinea pigs of the chemical inducing bronchoconstriction to prostration of the guinea pigs by dyspnea, wherein the guinea pigs have bronchial sensitivities at least one and a half times greater than the mean of said measured time interval, and (b) brother-sister mating or selectively mating with their cousins or unrelated guinea pigs those hyposensitive guinea pigs identified in (a), so that the appearance rate for guinea pigs with said bronchial sensitivities is at least 90% in at least the fifth generation.

22. The method of claim 21, wherein the mating is carried out so that the appearance rate for guinea pigs with said bronchial hyposensitivities is 100% in at least the sixth generation.

23. The method of claim 21, wherein the guinea pigs are Hartley-strain guinea pigs.

24. The method of claim 21, wherein the chemical inducing bronchoconstriction is acetylcholine or histamine.

* * * * *